United States Patent [19]

Fontanges

[11] 4,195,076
[45] Mar. 25, 1980

[54] PROCESS FOR THE PREPARATION OF HEMAGGLUTININ FROM VIRAL SOURCES AND METHODS OF UTILIZING SAME

[75] Inventor: Robert Fontanges, Lyon, France

[73] Assignee: Science Union et Cie, Societe Francaise de Recherche Medicale, Suresnes, France

[21] Appl. No.: 945,317

[22] Filed: Sep. 25, 1978

Related U.S. Application Data

[62] Division of Ser. No. 553,293, Feb. 26, 1975, Pat. No. 4,136,168.

[30] Foreign Application Priority Data

Mar. 5, 1974 [FR] France .............................. 74 07352

[51] Int. Cl.² ...................... A61K 9/12; A61K 39/18; C12B 1/00

[52] U.S. Cl. ...................................... 424/43; 195/29; 424/45; 424/89; 435/69

[58] Field of Search .................. 195/2, 4, 29; 424/89, 424/43, 45

[56] References Cited

PUBLICATIONS

Brand et al., Chem. Abst., vol. 77 (1972), p. 124,621n.
Becht et al., Chem. Abst., vol. 78 (1973), p. 82,798p.

*Primary Examiner*—Sam Rosen
*Attorney, Agent, or Firm*—Omri M. Behr

[57] ABSTRACT

This application relates to a process for producing two glycoproteins of viral origin. More specifically, it relates to a process for producing in a substantially pure form Neuraminidase and Hemagglutinin from the cultures of *Myxovirus Influenzae*. These glycoproteins find a therapeutical use as a mean for preventing or treating the flu.

16 Claims, No Drawings

4,195,076

PROCESS FOR THE PREPARATION OF HEMAGGLUTININ FROM VIRAL SOURCES AND METHODS OF UTILIZING SAME

This is a division of application Ser. No. 553,293, filed 2/26/75, now U.S. Pat. No. 4,136,168.

DESCRIPTION OF THE PRIOR ART

The relevant prior art may be illustrated by the following publications:
Skehel—Nature—Newbiology 238 (1972) 145
Reginster—Acta Viro. 9, 470 (1965)

SUMMARY OF THE INVENTION

This invention relates to a new process for obtaining viral proteins from cultures of *Myxovirus Influenzae*.

More precisely, the invention relates to a process for producing and recovering viral Hemagglutinin and viral neuraminidase in substantially pure state. The process is performed in submitting cultures of strains of *Myxovirus Influenzae* and namely strain of Hong-Kong virus $A_2/68$ ($H_3N_2$) to the action of proteolytic enzymes obtained from cultures of *Streptomyces fradiae*, concentrating the fractions by diafiltration, separating the pure components by centrifugation in a discontinuous gradient of density in the presence or absence of a tensio-active agent and recovering successively viral Neuraminidase and viral Hemagglutinin. Analysis of these pure fractions shows a glycoproteinic structure. The thus obtained glycoproteins may be used in the treatment or prevention of the flu in human or veterinary medicine. They are incorporated in pharmaceutical compositions either separately or in combination, in admixture with a pharmaceutical inert non-toxic carrier suitable for parenteral, rectal, sublingual or permucous administration.

The invention also relates to a method for preventing or curing warm-blooded animals exposed or contaminated by *Myxovirus Influenzae*.

PREFERRED EMBODIMENTS

The object of this invention is to obtain, by a new process, viral proteins from the 'flu virus.

It is known that the envelope of *Myxovirus Influenzae* contains at least two specific glycoproteins which may be isolated either by the action of detergents, or by the action of protease, or by the combined action of both reagents.

However, a recent publication of Skehel (Nature— New Biology 238 (1972) 145) has shown that treatment with a protease, whilst ensuring separation of these two constituents of the virus envelope, causes complete breakdown of the viral Neuraminidase. The other glycoprotein or Hemagglutinin obtained under these conditions, is partially denatured, although found in the crystalline form, and thus loses its hemagglutinating properties. Therefore, it is very interesting to isolate and make available these two purified glycoprotein fractions, for they constitute a precious antigenic material, which permits one to consider vaccination against flu either by administration of hemagglutinin or viral neuraminidase alone, or combining these two glycoprotein fractions to obtain a vaccine with broader antigenic properties.

It is also interesting to obtain a neuraminidase produced by the 'flu virus in a sufficiently pure and active form, for neuraminidase is the most stable genetic fraction of the flu virus. Furthermore, anti-neuraminidase virus antibodies formed under these conditions, without the possibility of inactivation of the flu virus, have nevertheless the property of reducing the importance or the severity of flu or reducing proliferation of the virus (Kilbourne, Journal of Virology 2 (1968) 281 and 778).

The present invention is thus a new process for producing the two glycoprotein fractions of virus origin, which permits one to obtain them in the pure state and ensures their separation without denaturation.

The present process consists in submitting the previously purified 'flu virus obtained from infected chick embryos or supporting cells, to the action of an enzyme or a mixture of proteolytic enzymes obtained from cultures of *Streptomyces fradiae*, concentrating the fractions containing the viral neuraminidase and hemagglutinin by diafiltration in aqueous solution on a selective permeable membrane with a reticulate structure, collecting the fraction retained by the cell membrane, then submitting the latter to breakdown by physical methods to collect successively a fraction containing mainly virus hemagglutinin, then a fraction containing mainly virus neuraminidase.

The process of the invention may also be defined by the following points:

(1) the enzyme or mixture of proteolytic enzymes is made up mainly by a protease isolated from cultures of *Streptomyces fradiae*, titrating at least 5000 Anson units per mg.

(2) the enzyme or mixture of proteolytic enzymes consists mainly of a protease isolated from cultures of *Streptomyces fradiae*, strains No. 1998 and No. 2019, from the collection of the National Museum of Natural History in Paris.

(3) the action of the enzyme or mixture of enzymes on the virus culture takes place at a temperature between 25° and 45° C.

(4) the action of the enzyme or mixture of enzymes on a viral culture is carried out at pH between 5 and 8.

(5) the action of the enzyme or mixture of enzymes is carried out for a duration between 1 and 7 hours.

(6) the concentration of the enzyme or mixture of enzymes varies between 1 and 30%.

(7) the separation of the protein fractions after diafiltration is carried out by centrifugation in a discontinuous density gradient.

(8) the discontinuous density-gradient is obtained from aqueous solutions of sodium glutamate, the concentrations of which vary between 1 and 40% containing a tensio-active agent such as sodium dodecyl sulphate at a concentration of 0 to 2%.

(9) a variant of the process of the invention, which consists in the prolongation of the enzyme action on virus cultures causing a breakdown of the hemagglutinin and permitting one to obtain only one glycoprotein fraction consisting essentially of viral neuraminidase.

(10) the strain of 'flu virus used preferably for culture was the Hong-Kong virus $A_2/68$ ($H_3N_2$), the NWS strain of virus $A_0$, the mutant of strain RI/5+ of virus $A_2$, and strain $A_3$-XL of the virus $A_2$.

The procedure was also applicable to other strains of the 'flu virus, for example, the human $A_2$ virus/Singapore/1/57; the virus $A_2$/England/52/64; the virus $A_2$/England/76/66 or the recombined X-7 (F-1).

The invention extends also to neuraminidase of viral origin obtained according to the process defined above. It may be extended more particularly to neuraminidase of virus A$_2$/Hong Kong/68 (H$_3$N$_2$) obtained according to the process defined above.

It may also be extended to hemagglutinin of viral origin obtained by the procedure defined above and more particularly hemagglutinin of virus A$_2$/Hong Kong/68 (H$_3$N$_2$) obtained according to the procedure defined above. The invention concerns also the use as a drug of neuraminidase of viral origin whenever obtained by the procedure of the invention, which may be used in the prophylaxis or treatment of 'flu, in warm blooded animals.

Neuraminidase may be used alone with an inert pharmaceutical carrier or in combination with Hemagglutinin of viral origin. Neuraminidase may also be used in combination with bacterial adjuvents which strengthens the antigenic power of said glycoprotein.

As bacterial adjuvent, they may be utilized pure or raw proteins obtained from cultures of staphylococci, Neisseria, Klebsiella or micrococci. For this purpose, the neuraminidase, obtained according to the procedure of this invention, from cultures of the 'flu virus, is presented in the form of pharmaceutical preparations, more particularly solid, liquid or gaseous preparations for aerosols with a gaseous propellent such as butane or a freon, suitable for parenteral, sublingual, rectal or permucous administration. The neuraminidase obtained according to the above defined process is administered preferably in the form of an aerosol formulation containing an aqueous diluent gaseous propellent.

The usual posology depends on the age or weight of the patient, and the number of administrations per day.

More frequently the thus obtained glycoproteins are administered for two to four days and the administration is renewed two to four times after one week each time of interruption.

The following examples illustrate the invention. They are not limitative.

EXAMPLE 1

One inoculates 200 chick eggs fertilised 11 days previously with 0.2 ml per egg of the virus suspension of the A$_2$/Hong Kong/68 (H$_3$N$_2$) 'flu virus in buffered physiological saline at a concentration of 1/1000.

After 48 hours incubation, one collects about 900 ml of infected allantoic fluid with a concentration of about 2050 hemagglutinating units and 130 neuraminidasic units/ml. One then proceeds to a first separation by centrifugation at 5000 g for ½ hour to eliminate cell debris and mucoprotein. The supernatant fluid is then centrifuged at 105 000 g for 2 hours maintaining the temperature at about 4° C. The sediments obtained by centrifugation are mixed together and suspended in isotonic saline. The suspension thus obtained is submitted for 3 minutes to the action of ultra-sounds (12 K cycles). One then collects a suspension containing 12,000 hemagglutinating units per ml and 190 neuraminidase units per ml. 20 ml of this virus suspension are then removed and the protease of *Streptomyces fradiae* at a concentration of 1 mg/ml is added. One leaves this in contact at 37° C. for 2 hours. The mixture is then concentrated by diafiltration on a Diaflo diafiltration cell retaining the molecules of molecular weight greater than 10 000 with regard to distilled water.

One then collects in the cell 9 ml of a concentrated solution containing 280 units of neuraminidase/ml.

One then removes three times 7.5 ml of this solution which are placed in three discontinuous gradients of 28 ml of solutions of sodium glutamate, the concentration of which ranges from 5 to 40%. One then centrifuges for 30 hours at 24 000 cycles/minute maintaining the temperature at 10° C. On removal from the centrifuger 1.2 ml fractions are collected and treated using an analyser made by ISCO (model 640).

Thus, they are collected 3 successive gradients with one gradient for each lot, thus three times 3 ml of the solution containing substantially neuraminidase. These 9 ml contain approximately 750 units of neuraminidase and correspond to 20 ml of the virus suspension treated with the proteolytic enzyme. The collection of other peaks allows the obtention of the hemagglutinin.

The neuraminidasic activity expressed in units is determined by measuring the quantity of neuraminic acid liberated according to Warren's method modified by C. Bottex, G. Chatot and R. Fontanges using young horse serum as substrate. The hemagglutinin levels are determined by hemagglutination methods using chick and human O (Rh+) red cells.

The protease of *Streptomyces fradiae* used here, fulfills the following analytical norms:

| | |
|---|---|
| total proteolytic activity | 7000 Anson U/mg |
| Proteolytic activity not inhibited by iniprol | 5610 Anson U/mg |
| Proteolytic activity not inhibited by the trypsin-inhibitor extracted from soja beans | 5570 Anson U/mg |
| Protein content (Lowry's method) | 45.7% dry weight. |
| Enzyme-electrophoresis | prepondernace of component 2. |

It is obtained after culture of *Streptomyces fradiae* and drying of the culture medium, by absorption on an ion-exchange resin followed by fractionated elution.

EXAMPLE 2

Influence of the enzyme concentration on the kinetics of liberation of hemagglutinin and neuraminidase of virus origin.

| | ENZYMATIC KINETICS | | |
|---|---|---|---|
| Proteolytic Enzyme | Time to obtain an optimum concentration of hemagglutinin | Time to obtain an optimum concentration of neuraminidase | Optimum of concentration of enzyme |
| Bromelain 1 mg/ml (+ 4° C.) | 3 h | 30 mn | 1% |
| Bromelain 1 mg/ml (37° C.) | 30 mn | 30 mn | 1% |
| Trypsin 1 mg/ml (+ 37° C.) | 30 mn | 30 mn | 1% |
| Alpha chymotrysin 1 mg/ml (+ 37° C.) | 30 mn | 60 mn | 5% |
| Enzymes obtained from S. Fradiae 1 mg/ml (+ 37° C.) | 60 mn | 60 mn | 10% |

The enzyme obtained from cultures of *Streptomyces fradiae* is that which permits one to obtain very rapidly maximum liberation of both virus proteins with the lowest possible concentration of enzyme.

EXAMPLE 3

Influence of time of contact of the proteolytic enzyme on the possibilities of separation of virus neuraminidase and hemagglutinin after centrifugation in an discontinuous density gradient.

GRADIENTS OF POTASSIUM TARTRATE AT CONCENTRATIONS FROM 1 TO 40%

Centrifugation: 20 h at 10° C.
Deposit 2.5 ml of treated virus suspension

| Contact time virus - protease | 1 H | 3 H | 5 H | 20 H |
|---|---|---|---|---|
| Bromelain 1 mg/ml (+ 4° C.) | | | Heuraminidase alone | Neuraminidase alone |
| Bromelain 1 mg/ml (+ 37° C.) | + | | | ++ |
| Trypsin 1 mg/ml 10% (+ 37° C.) | Neuraminidase alone | | | +++ |
| Enzymes obtained from cultures of S. fradiae 1 mg/ml 5% at 37° | | +++ | | +++ |
| at 10° | + | ++ (30 h centrifugration) | | +++ |

+++ very good separaton of neuraminidase and hemagglutinin
++ average separation
+ partial separation

EXAMPLE 4

Activity of proteolytic enzymes to liberate NA and HA from A₂ Hong Kong Virus (NA=neuraminidase and HA=hemagglutinin)

The resultants express the quantities of HA and NA liberated in relation to the titers of initial virus and for an optimum contact time between virus and protease.

| | HA liberated | % of NA liberated |
|---|---|---|
| Bromelain 4° | × 12 | 1% |
| Bromelain 37° | × 2 | 1% |
| Trypsin 37° | × 8 | 5% |
| Alpha-chymotrypsin 37° | × 3 | 2% |
| Raw enzymes obtained from S. fradiae 37° | × 5 | 5% |
| Purified enzymes obtained from S. fradiae 37° | × 10 | 8% |

Thus, it would appear from this table that the enzymes obtained from cultures of *Streptomyces fradiae* allow one to obtain the highest concentrations of neuraminidase and hemagglutinin from the virus.

EXAMPLE 5

The operative method is that of example 1 slightly modified. One inoculates under similar conditions 200 chick eggs with a suspension of 'flu virus ($A_2$/Hong Kong/68/$H_3N_2$). After two days incubation, one collects 1500 ml of infected allantoic fluid with a titer of 4000 hemagglutinating units per ml and 350 neuraminidase units per ml corresponding to liberation of 0.107 g of sialic acid per ml. One then carries out a double centrifugation and the centrifugal deposit was placed in suspension in a phosphate buffer. One obtains 500 ml of the purified virus suspension containing 12 000 hemagglutinating units per ml and 520 neuraminidasic units per ml, corresponding to the liberation of 0.157 g of sialic acid per ml. One then removes aliquot parts of this suspension and submits them to the action of the proteases of *Streptomyces fradiae* at 37° for two hours. These fractions were then reunited and concentrated by diafiltration to 60 ml. These 60 ml were divided up into six 10 ml-fractions deposited on 6 successive gradients of sodium glutamate and at concentrations ranging from 5 to 40%, to which one adds 1% sodium dodecyl succinate.

One collects after diafiltration 60 ml of the virus suspension thus treated, concentrated and purified, with a titer of 48 000 hemagglutinating units per ml and 710 neuraminidasic units per ml, corresponding to the liberation of 0.212 mg of sialic acid per ml.

After centrifugation at 60000 g for 30 hours at +15°, one collects, on six occurances 144 ml of suspension with a titer of 1600 hemagglutinating units per ml, i.e. in all 228,000 units and 48 ml of a suspension containing 310 neuraminidasic units per ml, i.e. in all 13 800 neuraminidasic units.

The suspension were then divided up on a sephadex G 15 column in order to retain impurities, such as sodium glutamate and sodium dodecyl succinate. The fractions obtained possess activities roughly identical to those mentioned above.

Finally, from 1500 ml of infected allantoic fluid, it was thus possible to obtain a high yield of the purified hemagglutinin fraction and a purified neuraminidasic fraction.

Analysis of the thus obtained sub-units by electrophoresis on a gel of polyacrylamide does not reveal any contamination of the Hemagglutinin sub-unit with Neuraminidase and vice-versa. The infra-red spectrum (KBr) of each sub-unit show characteristic stretchings in the neighbourhood of 3μ and 9.5μ, reflecting the glycoproteinic structure of both sub-units. The infra-red spectrum of the hemagglutinin sub-unit is similar to this of the neuraminidase sub-unit; however, the peak at 3.5μ—corresponding to the stretchings of the methylene groups is much more important than in this of neuraminidase; moreover, a shoulder at 3.6μ evidences the presence of associated valency stretchings O-H.

What I claim is:

1. A process for the obtention of viral proteins from flu virus by submitting cultures of *Myxovirus Influenzae* to the action of an enzyme or a mixture of proteolytic enzymes obtained from cultures of *Streptomyces fradiae*, concentrating the fractions including neuraminidase and hemagglutinin by diafiltration in aqueous solution on a selectively permeable membrane with a reticulate structure capable of retaining molecules of molecular weight exceeding 10,000 to form a concentrate of a material having a molecular weight in excess of 10,000, collecting the concentrate retained by the membrane of the diafiltration cell, then submitting said concentrate to fractionation by physical methods to collect the fraction containing substantially the viral hemagglutinin.

2. A process for the preparation of hemagglutinin from *Myxovirus Influenzae* which comprises the steps of:

(a) suspending said virus in saline to form a viral suspension;
(b) treating said viral suspension with protease produced by *Streptomyces fradiae* to form a lysed suspension;
(c) subjecting said lysed suspension to diafiltration through a semi-permeable membrane capable of retaining molecules of molecular weight exceeding 10,000 to form a concentrate of material having a molecular weight in excess of 10,000;

(d) subjecting said concentrate to discontinuous density gradient centrifugation;

(e) isolating the centrifugate fractions containing hemagglutinin.

3. A process according to claim 2 in which the protease produced by the cultures of *Streptomyces fradiae* titrates at least, 5000 Anson units/mg.

4. A process according to claim 2 in which the action of the protease on the virus culture occurs at a temperature between 25° and 45° C.

5. A process according to claim 2 in which the action of the protease on the virus culture is carried out at a pH ranging from 5 to 8.

6. A process according to claim 2 in which the action of the protease on the virus culture is carried out for a duration ranging from 1 to 7 hours.

7. A process according to claim 2 in which the enzyme concentration of protease varies from 1 to 30%.

8. A process according to claim 2 in which the discontinuous density gradient was obtained using solutions of sodium glutamate having a concentration from 1 to 40%.

9. A process according to claim 2 in which the discontinuous density gradient was obtained using solution of sodium glutamate incorporating from 0.5 to 2% of a surface active agent.

10. A process according to claim 2 in which the surface active agent is sodium dodecyl sulphate.

11. A process according to claim 2 in which the strain of *Myxovirus influenzae* was the Hong-Kong virus A/68 (H$_3$N$_2$) strain.

12. The hemagglutinin of viral origin whenever obtained by the process of claim 2.

13. The hemagglutinin of virus A/Hong-Kong/68 (H$_3$N$_2$) whenever obtained by the process of claim 11.

14. A method for preventing or curing influenza in warm-blooded animals which consists in administerating to said warm-blooded animals exposed to contamination by the 'flu viruses an effective amount of the Hemagglutinin of viral orgin of claim 12 or claim 13.

15. A composition comprising a pharmacologically effective amount of hemagglutinin of claim 12, and a pharmacologically acceptable inert excipient.

16. A pharmaceutical composition according to claim 15 in the form of a preparation for aerosol containing a gaseous propellant in admixture with the active ingredient.

* * * * *